United States Patent [19]
Rohwedder

[11] Patent Number: 5,421,206
[45] Date of Patent: Jun. 6, 1995

[54] METHOD AND APPARATUS FOR MECHANICAL STRENGTH TESTING OF COMPONENTS

[75] Inventor: Arnim Rohwedder, Fuerth, Germany

[73] Assignee: Siemens Aktiengesellschaft, Munich, Germany

[21] Appl. No.: 277,581

[22] Filed: Jul. 20, 1994

[30] Foreign Application Priority Data

Aug. 16, 1993 [DE] Germany ............... 43 27 509.5

[51] Int. Cl.⁶ .......................................... G01N 29/00
[52] U.S. Cl. ........................................ 73/834; 73/821
[58] Field of Search ............. 73/834, 821, 119 R, 73/119 A, DIG. 1, 662, 644

[56] References Cited

U.S. PATENT DOCUMENTS

| | | | |
|---|---|---|---|
| 4,348,904 | 9/1982 | Bautista, Jr. ................ | 73/644 |
| 4,640,131 | 2/1987 | Kröning et al. . | |
| 4,669,472 | 6/1987 | Eisenmenger . | |
| 4,674,505 | 6/1987 | Pauli et al. . | |
| 4,721,106 | 1/1988 | Kurtze et al. . | |
| 4,760,731 | 8/1988 | Bogatzki . | |
| 4,813,415 | 3/1989 | Reichenberger et al. ........ | 128/328 |
| 4,893,511 | 1/1990 | Voigt et al. . | |
| 5,078,149 | 1/1992 | Katsumata et al. .............. | 73/644 |
| 5,251,487 | 10/1993 | Marshall ...................... | 73/644 |
| 5,309,897 | 5/1994 | Hassler et al. .................. | 601/4 |

FOREIGN PATENT DOCUMENTS

| | | |
|---|---|---|
| 354146 | 5/1979 | Austria . |
| 1904864 | 9/1969 | Germany . |
| 3307462 | 9/1984 | Germany . |
| 3441805 | 5/1986 | Germany . |
| 4224209 | 1/1993 | Germany . |
| 1163199 | 6/1985 | U.S.S.R. . |

OTHER PUBLICATIONS

"Possibilities of Automatic Ultrasonic Testing of Welded Automobile Hollow Valves," Knopf, Materials Testing, vol. 11, No. 9, Sep. 1969, pp. 293–297.

"The Acoustic Impact Technique–A versatile Tool for Nondestructive Evaluation of Aerospace Structures and Components," Schroeer et al., Materials Evaluation, Nov. 1970, pp. 237–243.

"Meyers Lexikon der Technik und der exakten Naturwissenschaften," vol. 2, p. 944 and vol. 3, pp. 2739–2740.

Primary Examiner—Richard E. Chilcot, Jr.
Assistant Examiner—Eric S. McCall
Attorney, Agent, or Firm—Hill, Steadman & Simpson

[57] ABSTRACT

In a method and apparatus for the mechanical strength testing of components with respect to a strength criterion an acoustic pulse in the form of an acoustic shockwave is introduced into a component to be tested such that the shockwave is reflected acoustically with a polarity reversal at a reflection location before passing though a region of the component to be tested, thereby subjecting that region to tensile stress. The amplitude of the shockwave is selected such that the component is destroyed if it does not meet the strength criterion.

17 Claims, 4 Drawing Sheets

METHOD AND APPARATUS FOR MECHANICAL STRENGTH TESTING OF COMPONENTS

BACKGROUND OF THE INVENTION

1. Field of the Invention

The present invention is directed to a method and to an apparatus for testing the mechanical strength of components with respect to a predetermined strength criterion. The strength criterion indicates, for example, the amplitude and/or the chronological curve and/or the direction and/or the nature (for example, the polarity of applied pressure or tension), etc., of a mechanical stress that faultless components must withstand.

2. Description of the Prior Art

In conventional methods for testing mechanical strength, forces must usually act on the component to be tested. The problem arises that plastic deformations of the component occur, particularly in the region of the location at which the force is introduced, even when the component meets the strength criterion, when the forces applied for testing lie only slightly below those forces—in terms of their strength—that would lead to the destruction of the component. As a result, it is no longer possible to employ the component for its intended purpose. Consequently, every individual component cannot be subjected to the strength testing. On the contrary, only spot checks can be undertaken. In many instances, particularly given components whose failure involves serious consequences, it would be desirable to be able to test every individual component with respect to the strength criterion.

A method of the general type initially set forth is disclosed in German PS 36 20 637 which can alleviate this problem since the component to be tested is charged with a pulse dimensioned such that a component that does not meet the respective strength criterion is destroyed due to the influence of the pulse. Component can only be tested, however, using this known method, with respect to strength criteria related to compression stressing.

SUMMARY OF THE INVENTION

It is an object of the present invention to provide a method of the type initially generally described as well as an apparatus for the implementation of this method wherein damage, for example deformation, to those components that meet the strength criterion is precluded and wherein the components can nonetheless be tested with respect to strength criteria related to tensile stresses.

This object is inventively achieved in a method for mechanical strength testing of components with respect to a predetermined strength criterion, wherein a positive acoustic pressure pulse is introduced into a component to be tested and the pressure pulse is reflected acoustically with a polarity reversal at a reflection location before traversing a region of the component to be tested for tensile stressing and thus, upon propagating in that region, subjecting the region to tensile stress. The amplitude of the pressure pulse is selected such that the component is destroyed when the strength criterion is not met. Since the pressure pulse, which may be a shockwave, enters into the component to be tested without exerting any mechanical stresses whatsoever on the component to be tested, it is assured that a tested component can afterwards still be employed for its intended purpose, since no deformation or damage in the region of the location at which the force was introduced, i.e., in the region of the application location, occur. There is thus the possibility of subjecting each and every individual component to such a strength test. Those components that meet the strength criterion can thereby be reliably separated from those that do not meet the strength criterion, since the latter are destroyed by the pressure pulse. The mechanical stresses that thereby arise correspond directly to the local amplitude of the pressure pulse. The direction of the mechanical stressing is determined by the propagation direction of the pressure pulse. It is thus easily possible to select the characteristics of the pressure pulse such that the mechanical stressing required for testing with respect to the strength criterion is in fact exerted on the component. Even though a positive acoustic pressure pulse is introduced into the component to be tested, it is nonetheless possible also to subject the component to be tested to mechanical tensile stresses since, according to the invention, the pressure pulse is introduced such that it is reflected acoustically with a polarity reversal at a reflection location before passing though that region of the component to be tested for tensile stress. As is known, an acoustical reflection ensues at a boundary surface between a first medium and a medium having lower acoustic impedance, which causes a reversal of the polarity of the reflected wave compared to the incoming wave. The positive pressure pulse is thus reflected as a negative pressure pulse, with the result that tensile stresses are exerted on the component to be tested. When, after reflection at the reflection location, the pressure pulse reemerges from the component, it is preferable for the passage to ensue into a medium having an acoustic impedance which substantially corresponds to that of the material of the component, since significant mechanical stressings of the component at the exit location of the pressure pulse then do not occur. The method of the invention is also especially suited when surge-like loads must be exerted onto the component to be tested during the mechanical strength testing. This is easily possible by employing a pressure pulse having an amplitude curve corresponding to a suitably chronologically varying curve. Expediently, the pressure pulse is introduced into the component such that it enters into the component from a medium whose acoustic impedance substantially corresponds to that of the material of the component under test. It is thus assured that no significant reflection losses occur upon introduction of the pressure pulse into the component under test.

By contrast to known ultrasound testing methods employing a fatigue strength testing method with continuous sound having an ultrasound frequency matched to the resonant frequency of the component under test (see, for example, German OS 19 04 864), only a single pressure pulse is introduced into the component under test in the case of the invention.

According to a preferred modification of the invention, the pressure pulse is supplied to the component as a shockwave. As is known, a shockwave is a positive acoustic pressure pulse having an extremely steep leading edge. Upon introduction of a shockwave into the component under test, an impact-like pressure stressing is exerted on this component and an impact-like tensile stressing is exerted thereon after the polarity reversing reflection of the shockwave.

The method of the invention is particularly suited for testing valves made of ceramic that serve the purpose of controlling the entry and exit of gases in cylinders in an internal combustion engine, these valves being subjected to tensile stresses during operation. According to a version of the invention, it is provided in this context that the pressure pulse is preferably introduced into the valve at that end of the valve stem facing away from the valve disc such that its propagation direction substantially coincides with the longitudinal axis of the valve stem, and such that the pressure pulse is reflected with a polarity reversal, preferably at the end face of the valve disc. The mechanical tensile stresses required for the mechanical strength testing are thus exerted onto the valve stem.

As required, the amplitude of the pressure pulse can be increased by focusing it before introduction into the component under test, according to a modification of the invention.

An apparatus for the implementation of the method of the invention has a source that generates positive acoustic pressure pulses and a coupling medium, for example having the form of a coupling member, that conducts the pressure pulses to the component under test. An acoustic matching layer can be arranged between the coupling medium or member and the component under test, particularly when the acoustic impedance of the coupling medium or member differs substantially from that of the component. This acoustic matching layer has an acoustic impedance that is substantially the same as the material of the component. In order to achieve an optimum introduction of the pressure pulse into the component under test, it is provided in an embodiment of the invention that the coupling member has an application surface that is substantially congruent with the infeed location of the component under test and is arranged congruently with the infeed location for introducing the pressure pulse into the component under test, possibly with the interposition of the acoustic matching layer. When the pressure pulse is focused, it can be provided according to a modification of the invention that the coupling member correspondingly tapers in the direction toward the application surface.

For reflecting the pressure pulse with a polarity reversal at a reflection location before passing through a region of the component-under test, an apparatus part pressing against the component in the region of the reflection location is provided that exhibits a low acoustic impedance in comparison to that of the component. The polarity reversing reflection then ensues at the boundary surface between the component and the apparatus part. An a polarity reversing reflection can also be achieved, however, when the acoustic impedance of the apparatus part is substantially the same as that of the component and the apparatus part has a boundary surface to a medium whose acoustic impedance is lower than that of the component and than that of the apparatus part. The pressure pulse then enters into at least the apparatus part essentially reflection-free and is reflected with a reversal of polarity at the boundary surface thereof to the medium having low acoustic impedance. The reflected pressure pulse having reversed polarity proceeds back into the component under test essentially reflection-free. In a further modification of the invention, the apparatus part has a thickness measured in the propagation direction of the pressure pulse that is substantially less than the wavelength of the pressure pulse in the material of the apparatus part, and the apparatus has a boundary surface to a medium whose acoustic impedance is lower than that of the component. As a consequence of its lower thickness, the pressure pulse does not, so to speak, "perceive" the component and is reflected with a reversal of polarity at the boundary surface to the medium with low acoustic impedance. A special apparatus part for realizing the polarity reversing reflection is then superfluous when the component is accepted in the apparatus such that the component adjoins the atmosphere surrounding it, preferably the ambient air.

DESCRIPTION OF THE DRAWINGS

The invention shall be set forth below with reference to the figures of the attached drawings illustrating the example of testing a valve of ceramic serving the purpose of controlling the gas-changing process in internal combustion engines.

FIG. 1a shows the curve of a pressure pulse generated to conduct a test in the apparatus of FIG. 1.

DESCRIPTION OF THE PREFERRED EMBODIMENTS

FIG. I shows a valve generally referenced 1 that serves the purpose of controlling the gas-changing process in an internal combustion engine, this valve being manufactured of a ceramic material, for example aluminum nitride. The valve 1 is fashioned dynamically balanced and has a cylindrical valve stem 2, which in a known way merges at one end into an approximately conical valve disc 3. Valves of this type are used both in spark ignition engines and in diesel motors and are subjected to shock-like stresses when actuated with a camshaft or the like, particularly in the region of the valve stem 2. Tensile stresses that occur when closing the valve, and given a closed valve, are thereby especially critical for valves of ceramic materials.

Since, as is known, valve fractures lead to serious damage to the engine, potentially even to a total loss of the engine, it must be assured that the valves withstand the stresses which occur during operation. This is generally not a problem given valves manufactured of metallic materials. Given ceramic valves, however, even slight disturbances in the structure of the material lead to a failure of the valves. It is therefore not adequate to test individual valves for their mechanical strength in the manner of a spot check. On the contrary, each and every individual valve must be tested with respect to a strength criterion which, when met, guarantees that the valve is capable of withstanding the stresses that occur during operation. Of course, no damage to or modification of the valve that would be disadvantageous in the later employment thereof can be permitted to occur as a result of the testing.

In the method of the invention, a positive acoustic pressure pulse is therefore introduced into the valve I under test, the polarity, propagation direction, amplitude and chronological curve of the amplitude of this acoustic pressure pulse being selected such that the valve is destroyed if it does not meet the strength criterion.

Figure 1:
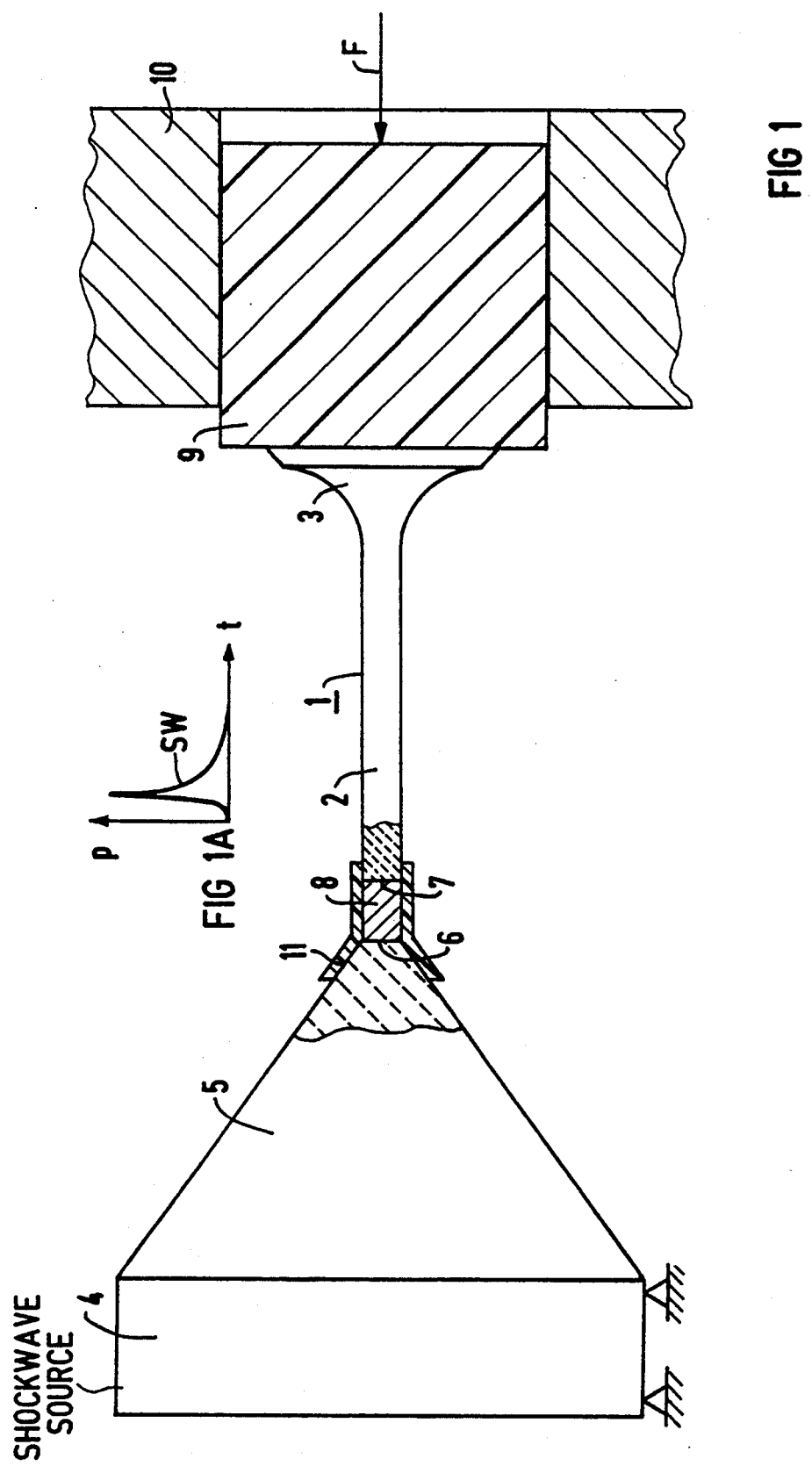
FIG. 1 is a schematic view, partly in section, of a valve accepted into a testing apparatus serving the purpose of implementing the method of the invention.

In the case of the method as implemented with the apparatus of FIG. 1, a focused shockwave is introduced into the valve 1 as a positive acoustic pressure pulse, such as a shockwave. The shockwave is generated with a shockwave source 4 schematically indicated in FIG. 1 that is stationarily seated. The shockwave 4 is an electromagnetic shockwave source as disclosed, for example, in U.S. Pat. No. 4,669,472, the disclosure thereof being incorporated herein by reference. The shockwave generated by the shockwave source 4 enters into a coupling member 5 that, for example, can be composed of steel, brass or ceramic. The coupling member 5 has a dynamically balanced, conical shape. Its cross-section at the end of the shockwave source essentially corresponds to the cross-section of a shockwave emerging from the shockwave source. As a consequence of the fact that the shockwaves are focused, the coupling member 5 can correspondingly conically taper, as shown.

The shockwave source of U.S. Pat. No. 4,669,472, moreover, already comprises a coupling member, which merely has to be fashioned of a material suitable for the present employment and has to have its end region facing away from the shockwave source shaped in conformity with the present employment. The coupling member 5, moreover, need not necessarily have a conical shape. Other shapes are possible as long as an undisturbed propagation of the shockwave is assured. The amplitude curve of the shockwave, i.e. the curve of the pressure p thereof over the time t, moreover, is schematically shown in FIG. 1a and is referenced SW.

In order to assure that no reflection losses occur upon entry of the shockwave into the valve 1, it must be assured that the shockwave enters into the valve 1 from a medium whose acoustic impedance substantially coincides with that of the material of the valve 1. No significant reflections then occur at the application location referenced 7 in FIG. 1. Either the coupling member 5 must itself be formed of a material whose acoustic impedance does not substantially deviate from that of the material of the valve 1 or, as shown in FIG. 1, an acoustic coupling (matching) member 8, that is composed of a material whose acoustic impedance substantially coincides with that of the material of the valve, must be arranged between the application surface 6 of the coupling member 5 and the application location 7 of the valve 1. In both instances, the shockwave then enters into the valve 1 from a medium whose acoustic impedance substantially coincides with that of the material of the valve 1.

The shockwave coupled into the valve stem 2 passes through the valve 1 in the direction of the longitudinal axis thereof and thereby exerts mechanical pressure stresses on the valve 1. Only the respective region of the valve 1 traversed by the shockwave is stressed.

In order to assure that the valve 1 is subjected to mechanical tensile stresses in the desired way, conditions for a polarity reversing reflection of the shockwave are created at the end face of the valve disc 3. The negative acoustic pressure pulse then occurring as consequence of the reversal in polarity arising in the reflection then passes through the valve 1 in the direction of the longitudinal axis thereof proceeding from the valve disc 3. The negative acoustic pressure pulse exerts tensile stresses on the valve, whereby, as a consequence of the described propagation direction of the negative acoustic pressure pulse, the stressing direction proceeds in the direction of the longitudinal axis of the valve 1 in the same way as during operation of the valve 1.

The amplitude of the shockwave generated with the shockwave source 4 is selected such that, taking unavoidable losses into consideration, the amplitude of the negative acoustic pressure pulse is of a height that generates tensile stresses whose level corresponds to a strength criterion that faultless valves must meet. Faultless valves thus survive the charging with the shockwave (i.e., with the negative acoustic pressure pulse) undamaged, whereas unusable valves are destroyed.

In the exemplary apparatus of FIG. 1, the conditions for a polarity reversing reflection at the end fact of the valve disc 3 are created by an apparatus part 9 adjacent the end face of the valve disc 3, with at least that region of the apparats part 9 which is adjacent to the valve 1 being formed of a material, for example rubber or plastic, whose acoustic impedance is substantially less than that of the ceramic material of the valve 1. The apparatus part 9, moreover, is accepted axially displaceably in a stationary guide part 10 and is charged (biased) with a force F proceeding in the direction of the longitudinal axis of the valve 1 with biasing means (not shown in FIG. 1), for example a spring, an electromagnet, pressure means or the like. As a result, the application location 7 of the valve is pressed against the application surface 6 of the application member 5, either directly or upon interposition of the acoustic coupling member 8. In order to avoid a falsification of the results of the testing process, the size of the force F is selected such that the static mechanical stresses occurring in the valve 1 as a consequence of the force F are at least one order of magnitude lower than the mechanical stresses that occur as a consequence of the charging with the shockwave or with the negative acoustic pressure pulse.

The acoustic coupling member 8, moreover, is attached to the application member 5 with a holder 11 formed, for example, of plastic.

In order to assure that the application surface 6 and application location 7, which have essentially the same diameters, are congruently arranged when the valve 1 is accepted in the apparatus, the section of the holder 11 which accepts the acoustic coupling member 8 has a length selected so that it acts as a centering means for the valve stem 2 in the way shown in FIG. 1.

Figure 2:
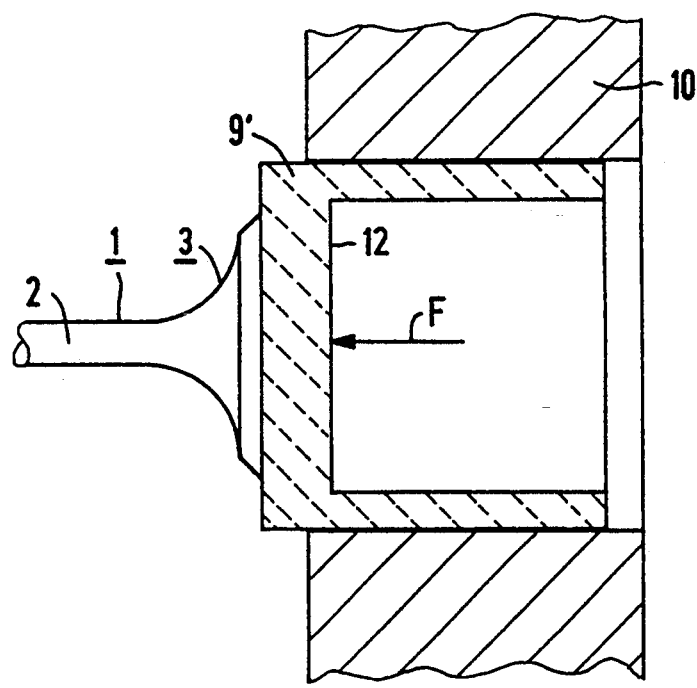
FIGS. 2-4 respectively show modifications of a detail of the apparatus of FIG. 1

According to FIG. 2, the conditions for a polarity reversing reflection can also be created by means of an apparatus part 9' composed of the same material as the valve 1. The apparatus part 9' is fashioned cup-shaped and that side 12 of its base facing away from the valve disc 3 adjoins a medium whose acoustic impedance is lower than that of the material of the apparatus part 9'. This medium in the apparatus illustrated in FIG. 2 is the ambient air. The shockwave emanating from the shockwave source 4 then runs through the valve stem 2 and the valve disc 3 essentially reflection-free into the base of the apparatus part 9 and is reflected acoustically soft at the rear side 12 thereof. Proceeding from the rear side 12, a negative pressure pulse then runs through the base of the apparatus part 9' entering essentially reflection-free into the valve disc 3 and stressing the valve 1 for tension in the way already set forth.

Figure 3:
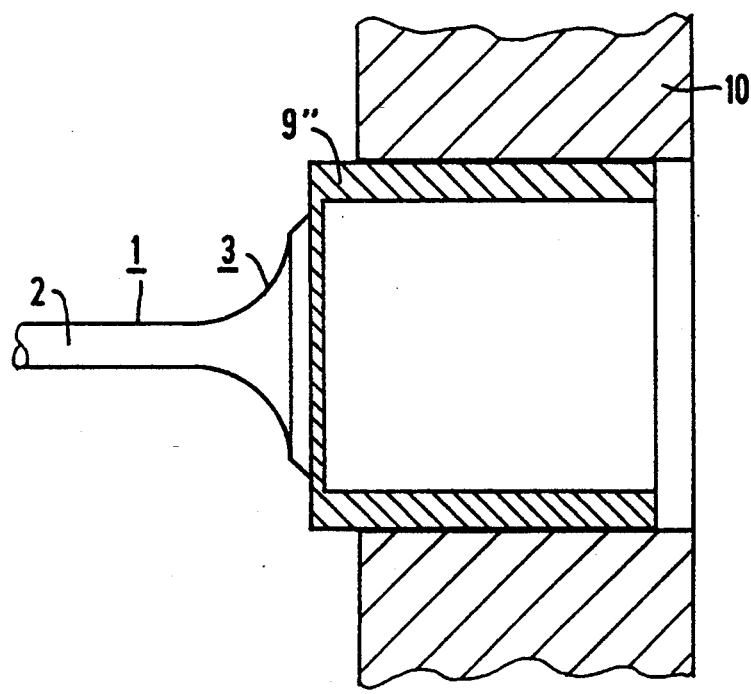

FIG. 3 shows another possibility of creating the conditions for a polarity reversing reflection. Here, the apparatus part 9" fashioned cup-shaped is composed of a material whose acoustic impedance is higher than that of the material of the valve 1. A polarity reversing reflection at the rear of the base of the apparatus part 9''', which again adjoins the ambient air, nonetheless occurs because the thickness of the base is substantially less, for example by an order to magnitude, than the wavelength of the fundamental wave of the shockwave in the material of the apparatus part 9'''. In this case, the shockwave or the negative acoustic pressure pulse which returns after the acoustically soft reflection does not, so to speak, "perceive" the base of the apparatus part 9'''.

Figure 4:
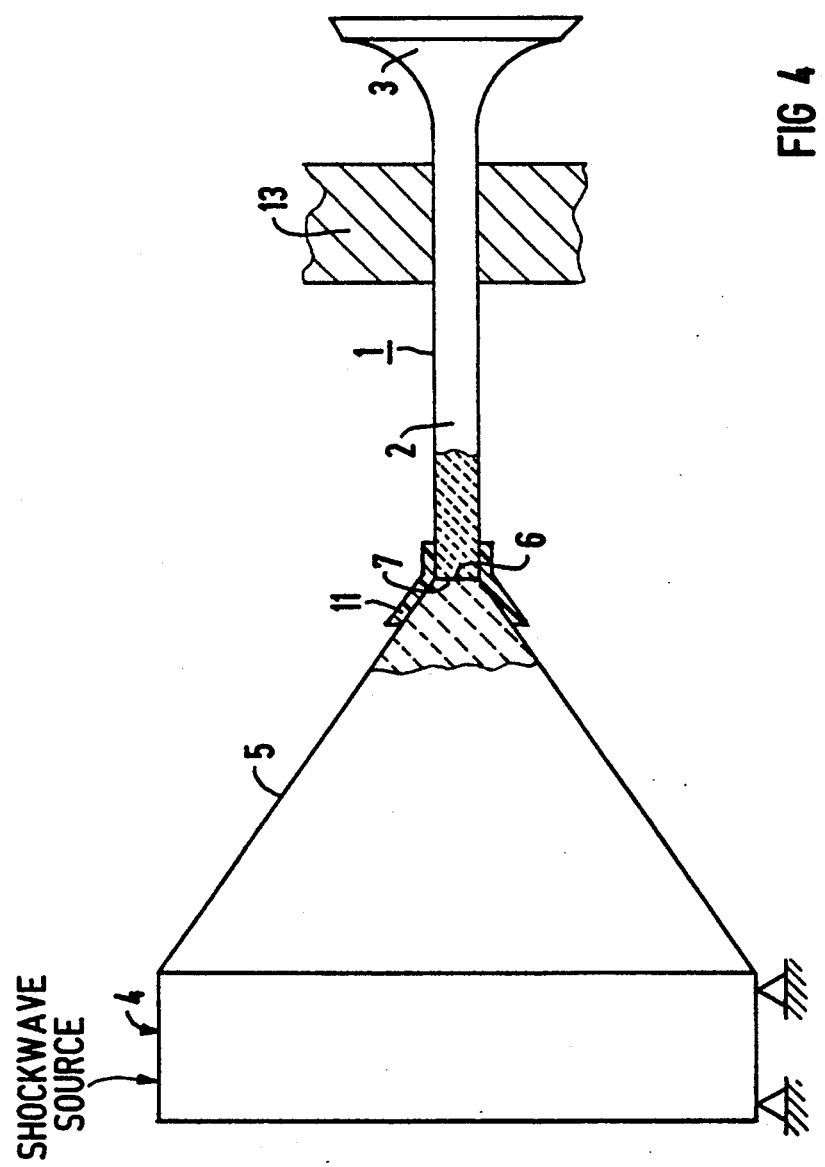

According to FIG. 4, however, the conditions for a polarity reversing refection at the end face of the valve disc 3 can also be created an arrangement wherein the valve 1 does not have its valve disc 3 adjoining an apparatus part but is instead held with clamp parts 13 in the region of its valve stem 2 so that the end face of its valve stem 2 serving as the application location 7 is directly adjacent against the application member 5, and the end face of the valve disc 3 adjoins a medium, namely the ambient air, whose acoustic impedance is lower than that of the material of the valve 1. Similar to the situation in the case of FIG. 1, the end face of the valve disc 3 here also forms the reflection location.

An acoustic coupling member, moreover, is not required in the case of FIG. 4 because the application member 5 is formed of a material whose acoustic impedance essentially corresponds to that of the material of the valve 1. The application member 5 is preferably composed of the same material as the valve 1.

Figure 5:
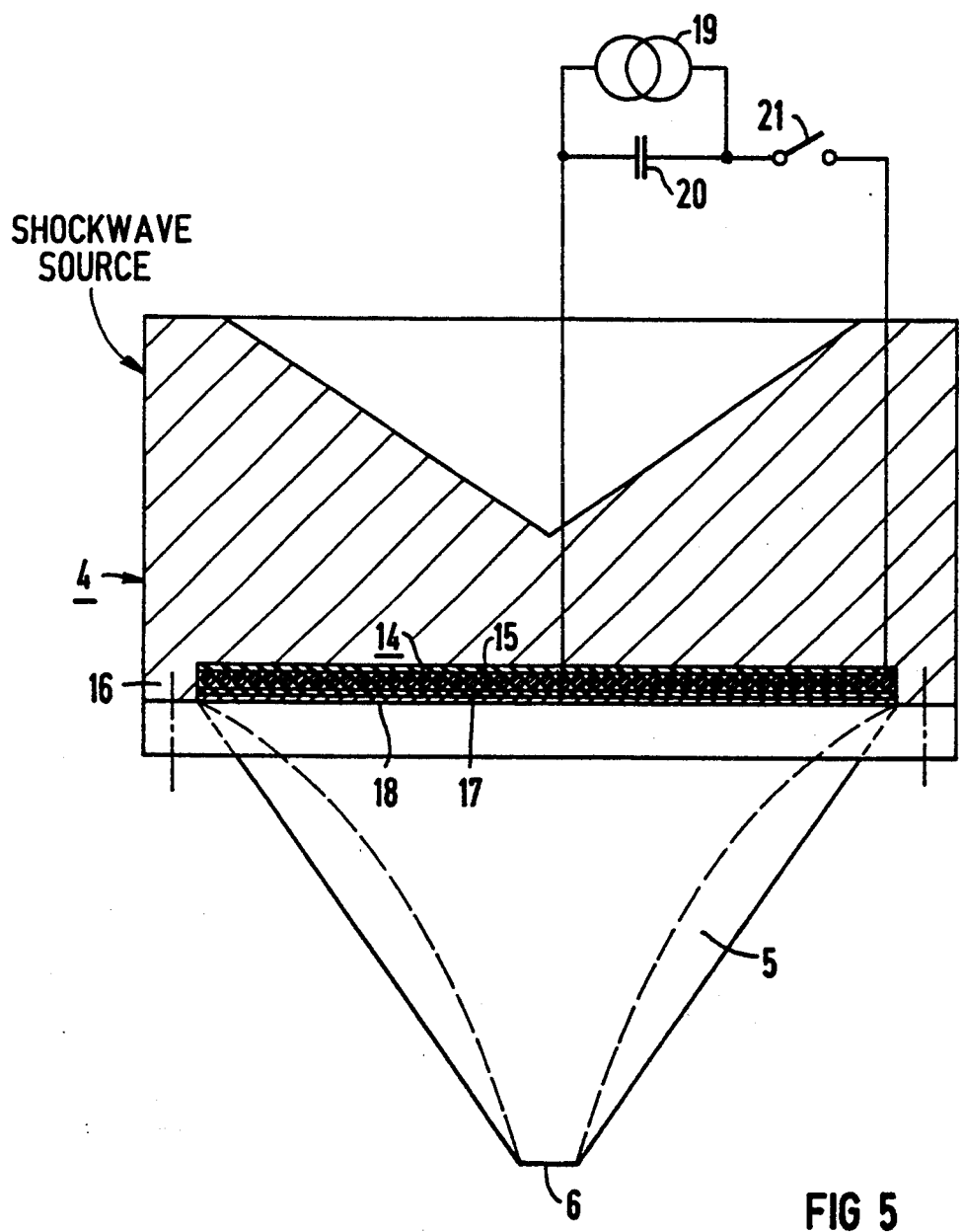
FIG. 5 is a schematic, sectional view of a source of acoustic waves suitable for employment in the apparatus of FIGS. 1-4.

FIG. 5 shows as special embodiment of a shockwave source 4 in greater detail. This is an electromagnetic shockwave source, as is known in a similar form in conjunction with medical shockwave lithotripsy and is disclosed, for example, in U.S. Pat No. 4,674,505 or U.S. Pat. No. 4,669,472. The shockwave source of FIG. 5 has a coil arrangement implemented as a flat coil 14 having helical turns, one thereof being referenced 15. The flat coil 14 is attached with an adhesive layer (indicated shaded) to a coil carrier 16 that is formed of a material having high acoustic impedance, for example ceramic. The end face of the coupling member 5 is arranged opposite the flat coil 14 and is separated therefrom by an insulating foil 17. If the coupling member 5 is manufactured of an electrically insulating material, for example ceramic, or a material having poor electrical conductivity, for example steel, this end face is provided with a thin layer 18 (indicated shaded) of a material having good electrical conductivity, for example silver. When the coupling member 5 is composed of a material having good electrical conductivity, for example copper, the layer 18 can be omitted. The coupling member 5 and the coil carrier 16 are pressed together with the assistance of screws—only the center lines of two screws are indicated—so that the end face of the coupling member 5 (potentially provided with the layer 18) presses flush against the flat coil 14 with the interposition of the insulating foil 17. In a way that is not shown, the interspaces between the turns 15 of the flat coil 14 are filled, moreover, with an electrically insulating casting resin.

The silver layer 17 can be planarly joined to the coupling member 5, preferably by plating or a similar method step. There is also the possibility of implementing the layer separately from the coupling member insofar as the layer is composed of an easily shapeable material such as, for example, silver and pressing this layer in between the coupling member 5 and the pancake coil 14 together with the insulating foil 17. As a consequence of the deformability of the layer 18, a good, planar seating of the layer 18 against the coupling member 5 then also is achieved.

For generating a shockwave, a high-voltage capacitor 20 is connected to a charging current source 19, and to the innermost turn and to the outermost turn of the flat coil 14, this high-voltage capacitor 20 being chargeable to voltages in the kV range. The capacitor 20 is discharged into the flat coil 14 by closing a high-voltage switch 21. As a result, eddy currents that are directed oppositely to the current flowing through the flat coil 14 are induced in the layer 18, or in the region of the coupling member 5 adjacent to the flat coil 14 when this region is formed of an electrically conductive material. The corresponding magnetic fields are thus oppositely directed, the result being that a mechanical pulse arises that proceeds into the application member and via the flat coil 14, into the coil carrier 16 of equal size. Since neither the dimensions of the coupling member 5 nor of the coil carrier 16 are small in comparison to the wavelength of the acoustic pressure pulse arising as a consequence of the mechanical pulse, these are not inertially accelerated. Instead, an acoustic wave in the form of a pressure pulse begins to propagate in the coupling member 5 and in the coil carrier 16. In order to avoid the dissociation of the flat coil 14, moreover, the coil carrier 16 should have a thickness that is greater than $\frac{1}{4}$ the wavelength of the fundamental wave of the pressure pulse generated in the material of the coil carrier 16. Further, it is expedient when the rear side of the coil carrier 16 proceeds non-parallel with reference to the front side thereof that carries the pancake coil 14, so that a scattering of the reflections occurs at the backside of the coil carrier 16. In the case of FIG. 5, the rear side of the coil carrier 16 is provided, for example, with a conical depression. A thickness of the coil carrier 16 that is greater than the length of the coupling member 5, as measured in wavelengths of the fundamental wave of the pressure pulse in the respective material, is not meaningful because a disturbing superimposition of a pressure pulse emitted directly into the coupling member 5 with portions of the same pressure pulse reflected at the coil carrier 16 no longer occurs in practice, given these length conditions.

The pressure pulse introduced into the coupling member 5 intensifies on its course in the coupling member 5, due to non-linear material properties, in a known way to form a shockwave, this being a pressure pulse having an extremely steep leading edge. As a consequence of the conical shape of the coupling member 5, a focusing of the pressure pulse occurs. The taper of the coupling member 5 in the direction toward the application surface 6, moreover, need not necessarily be conical, i.e. linear; as indicated with broken lines in FIG. 5, it can alternatively be exponential.

The shockwave source 4 of FIG. 5 differs from shockwave sources known in conjunction with lithotripsy in that an electrically conductive membrane, present as a separate component in the case of lithotripsy, is replaced by the layer 18. Of course, there is also the possibility of providing a separate membrane in the present case, this being pressed between the flat coil 14 and the coupling member 5.

An electromagnetic shockwave source, moreover, need not necessarily be employed for the implementation of the disclosed method. Other sources, for example piezoelectric, electrohydraulic or magnetostrictive sources can likewise be employed. Positive acoustic pressure pulses in the form of shockwaves thereby need not necessarily be generated. Positive acoustic pressure pulses in the form of what are referred to as ultrasound bursts, i.e. wave shapes that contain at least one period of, for example, a sinusoidal signal, can also be employed.

The focusing of the shockwaves or acoustic pressure pulses need not necessarily ensue by means of tapering the coupling member as described in FIG. 5. Alternatively, the focusing can be achieved in a known way by employing acoustic lenses (U.S. Pat. No. 4,674,505) and/or on the basis of sources that emit acoustic pressure pulses that are already focused as a consequence of their geometrical shaping (U.S. Pat. No. 4,669,477). Moreover, a coupling member is not absolutely necessary. There is also the possibility of applying the shockwaves or the acoustic pressure pulses to the component under test on the basis of a suitable coupling medium, for example by disposing the source of acoustic pressure pulses and the component under test in a bath of a suitable liquid. As is standard in conjunction with the medical application of acoustic pressure pulses, there is also the possibility of providing a flexible application cushion filled with a suitable coupling medium at the end of the shockwave source from which the shockwaves emerge.

An acoustic coupling member 8 that has an essentially constant cross-section over its length is employed in the described exemplary embodiment. If as the shockwaves acoustic pressure pulses are focused, however, there is also the possibility of employing an acoustic coupling member that likewise tapers according to the cross-sectional decrease of the focused shockwaves acoustic pressure pulses.

Although various minor modifications may be suggested by those versed in the art, it should be understood that I wish to embody within the scope of the patent granted hereon all such modifications as reasonably and properly come within the scope of my contribution to the art.

I claim as my invention:

1. A method for mechanical strength testing of a component with respect to a predetermined strength criterion, said method comprising the steps of:
   introducing a positive acoustic pressure pulse into a component to be tested;
   acoustically reflecting said pressure pulse with a polarity reversal at a reflection location to produce a negative pressure pulse;
   passing said negative pressure pulse through a region of said component to be tested and thereby subjecting said region to a tensile stress; and
   selecting an amplitude of said positive acoustic pressure pulse so that said component is destroyed if said component does not meet said strength criterion.

2. A method as claimed in claim 1, wherein said component has an acoustic impedance, and wherein the step of introducing said positive acoustic pressure pulse into said component comprises introducing said positive acoustic pressure pulse into said component from a medium having an acoustic impedance substantially corresponding to the acoustic impedance of said component.

3. A method as claimed in claim 1, wherein the step of introducing a positive acoustic pressure pulse into said component comprises introducing an acoustic shockwave into said component.

4. A method as claimed in claim 1, wherein said component comprises a valve used in a cylinder in an internal combustion engine for exchanging gas, said valve consisting of ceramic and having a valve stem with a longitudinal axis and a valve disc, and wherein the step of introducing a positive acoustic pressure pulse into said component comprises introducing a positive acoustic pressure pulse into said component along said longitudinal axis, and wherein the step of passing said negative pressure pulse through said region of said component to be tested for tensile strength comprises passing said negative pressure pulse through said valve stem along said longitudinal axis.

5. A method as claimed in claim 4, wherein said valve stem has an end facing away from said valve disc, and wherein the step of introducing a positive acoustic pressure pulse into said component comprises introducing a positive acoustic pressure pulse into said end of said valve stem facing away from said valve disc.

6. A method as claimed in claim 4, wherein said valve disc has an end face, and wherein the step of acoustically reflecting said pressure pulse with a polarity reversal comprises acoustically reflecting said pressure pulse with a polarity reversal at said end face of said valve disc.

7. A method as claimed in claim 1, comprising the additional step of focusing said pressure pulse before introducing said pressure pulse into said component.

8. An apparatus for mechanical strength testing of a component with respect to a predetermined strength criterion, said apparatus comprising:
   means for generating a positive acoustic pressure pulse;
   means for coupling said positive acoustic pressure pulse from said means for generating into a component to be tested and for causing said positive acoustic pressure pulse to propagate through said component;
   means for acoustically reflecting said pressure pulse with a polarity reversal at a reflection location for producing a negative pressure pulse and for causing said negative pressure pulse to propagate through a region of said component to be tested and for thereby subjecting said region to tensile stress; and
   said means for generating said positive acoustic pressure pulse generating a pressure pulse having an amplitude which causes destruction of said component if said component does not meet said strength criterion.

9. An apparatus as claimed in claim 8, wherein said means for coupling comprises a coupling member interposed between said means for generating a positive acoustic pressure pulse and said component.

10. An apparatus as claimed in claim 9, wherein said component has an acoustic impedance, and said apparatus further comprising an acoustic matching layer, having an acoustic impedance substantially corresponding to the acoustic impedance of said component, disposed between said coupling member and said component.

11. An apparatus as claimed in claim 9, wherein said component has an application location for said pressure pulses, and wherein said coupling member has an application surface which is substantially identical in size with a size of said application location.

12. An apparatus as claimed in claim 11, wherein said application surface is disposed substantially congruently with said application location.

13. An apparatus as claimed in claim 11, wherein said coupling member tapers in a direction from said means for generating a positive acoustic pressure pulse toward said application surface.

14. An apparatus as claimed in claim 8, wherein said component has an acoustic impedance, and wherein said means for acoustically reflecting said pressure pulse with a polarity reversal comprises an apparatus part disposed adjacent to said component at said reflection location, said apparatus part having an acoustic impedance which is low compared to said acoustic impedance of said component.

15. An apparatus as claimed in claim 8, wherein said component has an acoustic impedance, and wherein said means for acoustically reflecting said pressure pulse with a polarity reversal comprises an apparatus part having a first surface adjacent said component at said reflection location and having an acoustic impedance substantially the same as said acoustic impedance of said component, said apparatus part having a second surface, and a medium adjacent said second surface having an acoustic impedance which is lower than the acoustic impedance of said component and lower than the acoustic impedance of said apparatus part.

16. An apparatus as claimed in claim 8, wherein said component has an acoustic impedance, and wherein said means for acoustically reflecting said pressure pulse with a polarity reversal comprises an apparatus part having a first surface adjacent said component at said reflection location, said apparatus part having an acoustic impedance differing from the acoustic impedance of said component and said pressure pulse propagating in said apparatus part in a propagation direction at a propagation wavelength, said apparatus part having a second surface, spaced from said first surface by a distance in said propagation direction which is substantially less than said propagation wavelength, and a medium adjacent said second surface having an acoustic impedance which is lower than the acoustic impedance of said component.

17. An apparatus as claimed in claim 8, wherein said means for acoustically reflecting said pressure pulse with a polarity reversal comprises means for holding said component in ambient air at said reflection location.

* * * * *